United States Patent [19] [11] Patent Number: 4,567,177
Bigg et al. [45] Date of Patent: Jan. 28, 1986

[54] IMIDAZOLINE DERIVATIVES AS $\alpha_2$-ANTAGONISTS

[75] Inventors: Dennis Bigg, Jouy en Josas; Claude Morel, Magny-les-Hameaux; Mireille Sevrin, Paris, all of France

[73] Assignee: Synthelabo, Paris, France

[21] Appl. No.: 661,483

[22] Filed: Oct. 16, 1984

[30] Foreign Application Priority Data

Oct. 17, 1983 [FR] France ............................... 83 16474
Feb. 9, 1984 [FR] France ............................... 84 01997
Jun. 4, 1984 [FR] France ............................... 84 08726

[51] Int. Cl.⁴ ..................... A61K 31/55; A61K 31/47; C07D 471/06; C07D 487/06
[52] U.S. Cl. ................................. 514/214; 260/245.6; 514/294; 546/94
[58] Field of Search .......... 546/94; 260/239 G, 245.6; 548/218, 428; 424/256; 514/214, 294

[56] References Cited

U.S. PATENT DOCUMENTS 4,411,908 10/1983 Chapleo et al. ................ 548/348 X

FOREIGN PATENT DOCUMENTS 0109285 5/1984 European Pat. Off. .............. 546/94

OTHER PUBLICATIONS

Buehler and Pearson, *Survey of Organic Syntheses*, vol. I, Wiley & Sons 1977, pp. 836–837.
March, *Advanced Organic Chemistry*, 2d ed., McGraw Hill, pp. 422–423 and 1125.

*Primary Examiner*—Richard A. Schwartz
*Attorney, Agent, or Firm*—Wegner & Bretschneider

[57] ABSTRACT

Imidazoline derivatives of formula (I)

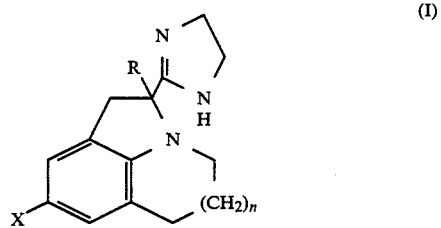

in which n is 1 or 2, R is hydrogen, $C_1$–$C_3$ alkyl or allyl group, and X is hydrogen, halogen atom, methyl or methoxy, in the form of enantiomers or mixtures thereof, and their pharmaceutically acceptable acid addition salts are useful as $\alpha_2$-antagonists.

4 Claims, No Drawings

IMIDAZOLINE DERIVATIVES AS α₂-ANTAGONISTS

The present invention relates to imidazoline derivatives, their preparation and pharmaceutical compositions containing them.

The imidazoline derivatives of the invention are of the formula I

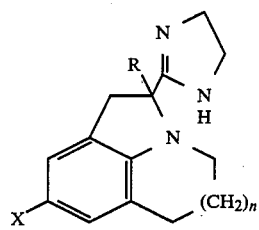

in which n is 1 or 2, R is hydrogen, $C_1$–$C_3$ alkyl or allyl, and X is hydrogen, halogen, methyl or methoxy.

The molecule of the imidazoline derivatives of the invention contains an asymmetric carbon atom so that they can therefore occur in the form of enantiomers or mixtures thereof. These various forms are part of the invention.

The imidazoline derivatives (I) can form addition salts with acids. These salts, especially if they are pharmaceutically acceptable, also form part of the invention.

The imidazoline derivatives (I) can be prepared according to the scheme given below:

French Patent No. 1,473,839 (cf. C.A. 68 (1968), 78164e).

According to the invention, the ester of formula (II), in which R' is $C_1$–$C_4$ alkyl and especially ethyl, is reduced by tin in the presence of hydrogen chloride to give the ester of formula (III).

If it is wished to obtain an imidazoline derivative (I) in which R is hydrogen, it is then possible to subject the ester (III) directly to the action of ethylenediamine in the presence of trimethylaluminium to form the imidazoline ring.

Otherwise this step is preceded by an alkylation, accomplished for example by the action of a compound of formula RY (R being as defined above and Y being a labile group such as an iodine or bromine atom) on the lithiated derivative prepared in situ by means of lithium diisopropylamide (butyllithium + diisopropylamine).

The alkylated ester of formula (IV) is then reacted with ethylenediamine as decribed above in relation to the compound of formula (III) to provide the imidazoline derivative (I).

The following Examples illustrate the invention. The structure of the compounds obtained was confirmed by analysis and IR and NMR spectra.

EXAMPLE 1

2-(4,5-Dihydro-1H-imidazol-2-yl)-1,2,5,6-tetrahydro-4H-pyrrolo[3,2,1-ij]quinoline and its fumarate (a) In a 1-liter three-necked flask, equipped with a reflux condenser and a hydrogen chloride gas inlet and placed in a bath of dry ice and isopropyl alcohol, there are introduced 24.7 g (0.108 mole) of ethyl 5,6-dihydro-4H-pyrrolo[3,2,1-ij]quinoline-2-carboxylate and 210 ml of absolute ethanol. Hydrogen chloride gas is condensed in until the starting ester has completely dissolved at a temperature of −20° C. 38.3 g (0.323 g-at.) of granulated tin is then added in a single portion. The reaction mixture is stirred at room temperature for 17 hours.

Scheme

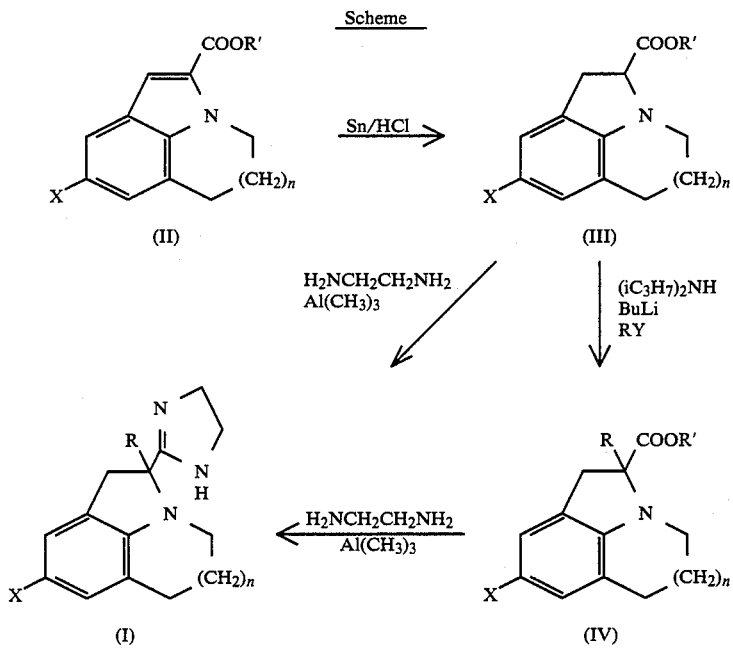

The starting esters (II) in which n is 1 and R' is $C_1$–$C_4$ alkyl can be prepared according to the method described for the methyl ester (R'=CH₃) by E. A. Steck et al., J. Heterocyclic Chem. 11 (3), 387–393 (1974).

The starting esters (II) in which n is 2 can be prepared in a similar manner from 2,3,4,5-tetrahydro-1H-benzazepine, described by P. E. Reyl and J. L. A. Rollet in The solution is concentrated and the oil and solid formed are taken up in 750 ml of absolute ethanol.

After the pH is brought to 9–10 by addition of ammonia gas, the tin salts formed are drained.

The ethanolic filtrate is concentrated to dryness, and the residue is taken up in iced water and extracted with diethyl ether. The extract is dried over sodium sulphate and concentrated to dryness under vacuum. Ethyl 1,2,5,6-tetrahydro-4H-pyrrolo[3,2,1-ij]quinoline-2-carboxylate is obtained in the form of an oil.

(b) Under argon, there are successively introduced into the flask 21 ml of toluene and 13.7 ml (0.032 mole) of 25.2% strength trimethylaluminium in hexane. The mixture is cooled in ice and 2.1 ml (0.032 mole) of ethylenediamine in 6 ml of toluene are added.

The mixture is stirred for 5 minutes and 4.6 g (0.02 mole) of ethyl 1,2,5,6-tetrahydro-4H-pyrrolo[3,2,1-ij]-quinoline-2-carboxylate, obtained as above, is then added at 50° C. in 18 ml of toluene.

The reaction mixture is heated to refluxing temperature. 18 ml of solvent is removed and the mixture is maintained at refluxing temperature for 12 hours.

The reaction mixture is cooled and 13.2 ml of water are added; the mixture is extracted with ethyl acetate and the organic phase is washed with sodium chloride solution and dried over sodium sulphate.

After filtering and concentration, the product is obtained, which is 2-(4,5-dihydro-1H-imidazol-2-yl)-1,2,5,6-tetrahydro-4H-pyrrolo[3,2,1-ij]quinoline.

This compound is converted directly to the fumarate, by reacting 4.2 g (0.018 mole) of the compound dissolved in 50 ml of ethanol with 1.97 g (0.017 mole) of fumaric acid dissolved in 100 ml of ethanol.

The mixture is stirred for 15 minutes and concentrated to dryness; the residue is taken up in acetone and the product filtered. After recrystallisation in ethanol, the compound melts at 186°–188° C.

EXAMPLE 2

2-Methyl-2-(4,5-dihydro-1H-imidazol-2-yl)-1,2,5,6-tetrahydro-4H-pyrrolo[3,2,1-ij]quinoline and its fumarate (a) The procedure is as in Example 1(a).

(b) In a 100-ml Keller flask, equipped with a magnetic stirrer, thermometer, argon inlet and dropping funnel and placed in a cold bath, there are introduced 1.7 ml (0.012 mole) of diisopropylamine and 10 ml of tetrahydrofuran, which are cooled to −75° C.

7.5 ml of a 1.6 M solution of butyllithium in hexane are then added in the course of 15 minutes.

The mixture is stirred for one hour at −75° C. and there are then added, in the course of 10 minutes, 2.1 g (0.009 mole) of the oil obtained as above dissolved in 7.5 ml of tetrahydrofuran.

Stirring is continued for a further hour and then, in the course of 10 minutes, there are added 7.1 g, equivalent to 3.1 ml (0.05 mole), of methyl iodide dissolved in 5 ml of tetrahydrofuran.

The mixture is stirred for 1 hour at −75° C. and is then allowed to return to approximately 0° C.

The mixture then poured into a mixture of water and ice, and extracted with ethyl ether in the presence of saturated sodium chloride solution. The organic phase is washed with water, dried, and evaporated under vacuum on a water bath. There remains a yellow oil which is purified by passing it through a column of silica, eluting with methylene chloride. A yellow oil is finally obtained which crystallises in the cold.

(c) In a 50-ml Keller flask, equipped with a magnetic stirrer, reflux condenser mounted on a Dean-Stark apparatus, thermometer, dropping funnel and argon inlet, there are introduced 10 ml of toluene and 5.4 ml (0.013 mole) of a 25% strength trimethylaluminium solution in hexane. The mixture is cooled by means of an ice bath.

0.9 ml (0.013 mole) of ethylenediamine dissolved in 3 ml of toluene is then added.

The mixture is stirred for 10 minutes at 0° C., then heated to 50° C. and has added thereto 2 g (0.0082 mole) of the oil obtained as above dissolved in 10 ml of toluene.

The mixture is then heated under reflux for 15 hours, then cooled to −10° C. and hydrolysed with 5.4 ml of water.

The mixture is stirred for 10 minutes, ethyl acetate is added, the inorganic material is separated and the organic phase is washed with saturated sodium chloride solution, dried over sodium sulphate and concentrated. There remains an oily, dark yellow compound which crystallises after several hours.

2.05 g of this compound is dissolved in 25 ml of ethanol and a solution of 0.8 g of fumaric acid in 50 ml of ethanol is added. The mixture is stirred, evaporated and washed with acetone, and the product is recrystallised in methanol. After being dried under vacuum, the fumarate melts at 184.5°–186° C.

EXAMPLE 3

2-(4,5-Dihydro-1H-imidazol-2-yl)-1,2,4,5,6,7-hexahydroazepino[3,2,1-hi]indole and its fumarate (a) In a 1-liter three-necked flask, equipped with a magnetic stirrer, thermometer and dropping funnel and placed in an ice bath, there are introduced 42.3 g (0.287 mole) of 2,3,4,5-tetrahydro-1H-benzazepine and 240 ml of 25% strength sulphuric acid. The mixture is allowed to cool to 0° C. and 20.7 g (0.3 mole) of sodium nitrite dissolved in 30 ml of water are then introduced dropwise in the course of 30 minutes.

A precipitate is formed which is stirred for 2 hours; the mixture is then extracted with methylene chloride, and the organic phase is separated, washed, dried and evaporated under vacuum on a water bath.

An oil is collected which is used, as it is, in the following step.

(b) In a 3-liter three-necked flask, equipped with a magnetic stirrer, reflux condenser, calcium chloride guard tube, thermometer and dropping funnel and placed under an atmosphere of argon, there are introduced 11.7 g (0.308 mole) of powdered lithium aluminium hydride and 400 ml of ethyl ether and, to the suspension obtained, there is added a solution of 49.3 g (0.279 mole) of the oil obtained as above in 600 ml of ethyl ether. The addition takes 1 hour, and the temperature is maintained at approximately 20° C. by an ice bath.

After 20 hours of reaction, there is formed a light precipitate which is dissolved by adding 500 ml of tetrahydrofuran. The mixture is then heated under reflux for 6 hours before being allowed to stand overnight at room temperature.

After being placed in an ice bath, the mixture is hydrolysed successively with 8 ml of water, 8 ml of 1N sodium hydroxide and 24 ml of water.

After 1 hour of stirring, the precipitate formed is drained and washed with tetrahydrofuran, and the filtrate is dried and evaporated under vacuum on a water bath. There remains a reddish oil which is used, as it is, in the following step.

(c) In a 500-ml flask, equipped with a magnetic stirrer, reflux condenser and calcium chloride guard tube, there are successively introduced 23.8 g (0.147 mole) of the oil obtained as above, 230 ml of absolute ethanol, 17.9 g (0.154 mole) of ethyl pyruvate and 15 drops of glacial acetic acid.

The mixture is heated under reflux for 1 hour and is then poured into a 2-liter flask containing ethanol saturated with hydrogen chloride gas.

The mixture is heated to boiling for 2 hours, and is then evaporated to dryness under vacuum on a water bath.

There remains a brown residue which is taken up with methylene chloride; the solution is washed with water, dried and evaporated again. There remains a resinous product which is purified by chromatography on silica, eluting with methylene chloride. A pale-yellow fairly mobile oil is finally collected.

(d) In a 500-ml three-necked flask, equipped with a magnetic stirrer, hydrogen chloride gas inlet, condenser with calcium chloride guard tube and thermometer and placed in an ice bath, there are introduced 8 g (0.0329 mole) of the ester obtained as above and 70 ml of ethanol.

The mixture is cooled to −20° C. and hydrogen chloride is condensed in at this temperature until an orange-red solution is obtained; the mixture doubles its volume. 11.9 g (0.1 g-at.) of granulated tin are then added in a single portion; the cold bath is removed and the mixture is stirred at room temperature.

After 26 hours of reaction, the mixture is evaporated under vacuum on a water bath. The residue is taken up in 250 ml of ethanol and the solution is cooled to −10° C. and ammonia is bubbled through it until a pH of 9 to 10 is attained.

The tin salts which have precipitated are drained and washed with iced ethanol and then ether; the organic phases are evaporated and the residue is treated with iced water and extracted with ether.

After being washed and dried, the ether phase is evaporated and a yellow oil is collected.

(e) In a 100-ml Keller flask, equipped with a magnetic stirrer, reflux condenser with calcium chloride guard tube, thermometer, argon inlet, dropping funnel and Dean-Stark apparatus, there are introduced successively 11 ml of toluene and 6.85 ml (0.16 mole) of a 25.2% strength suspension of trimethylaluminium in hexane.

The mixture is cooled by means of an ice bath, and a solution of 1.05 ml (0.016 mole), equivalent to 0.95 g, of ethylenediamine in 3 ml of toluene is added.

The mixture is stirred for 5 minutes and then heated; at about 50° C., there is added a solution of 2.45 g (0.01 mole) of the oil prepared as above in 9 ml of toluene. The mixture is then heated under reflux, removing approximately 8 ml of solvent, until an internal temperature of 110° C. is obtained. After 6 hours of heating, the mixture is cooled to approximately −15° C. and hydrolysed with 6.6 ml of water. The mixture is stirred for 10 minutes and extracted with ethyl acetate, and the organic phase is washed three times with saturated sodium chloride solution, dried over sodium sulphate and filtered; the solvent is evaporated. There remains a solid which melts at 138°–140° C., the fumarate of which is prepared directly.

For this purpose, 1.9 g (0.0079 mole) of the solid is dissolved in 25 ml of ethanol and the solution is filtered and mixed with a filtered solution of 0.8 g (0.0068 mole) of fumaric acid in 50 ml of ethanol.

The mixture is stirred for 15 minutes and concentrated to dryness under vacuum on a water bath, and the residue is taken up in acetone. Crystals are formed which are drained and rinsed with acetone. After drying under vacuum and recrystallisation in isopropyl alcohol, there remain yellow crystals which melt between 108° and 140° C.

EXAMPLE 4

2-(4,5-dihydro-1H-imidazol-2-yl)-2-methyl1,2,4,5,6,7-hexahydroazepino[3,2,1-hi]indole and its fumarate (a) In a 100-ml Keller flask, equipped with a magnetic stirrer, thermometer, argon inlet, dropping funnel and cooling bath, there are introduced, under argon, 2.3 ml (0.016 mole) of diisopropylamine and 15 ml of tetrahydrofuran; this solution is cooled to about −75° C., and 10 ml (0.016 mole) of 1.6M solution of butyllithium in hexane are then introduced in the course of 15 minutes.

The mixture is maintained at −75° C. for 1 hour, and 3.2 g (0.013 mole) of the hydrogenated ester obtained as described in Example 3d), dissolved in 10 ml of tetrahydrofuran, are then added in the course of 10 minutes.

Stirring is continued for a further 1 hour at −75° C., and 4.5 ml (0.072 mole), equivalent to 10.3 g, of iodomethane dissolved in 7 ml of tetrahydrofuran are then added in the course of 10 minutes.

Stirring is continued for a further 1 hour 30 minutes at −75° C., and the mixture is allowed to stand for a few hours in the refrigerator, still under argon.

The mixture is then poured into iced water and extracted with ethyl ether in the presence of saturated sodium chloride solution.

After washing, drying and evaporation of the organic phase, there remains an oil which is purified by chromatography on silica, eluting with methylene chloride.

(b) In a 50-ml Keller flask, equipped with a magnetic stirrer, reflux condenser with calcium chloride guard tube, thermometer, argon inlet, dropping funnel and Dean-Stark apparatus, there are introduced, under argon, 11 ml of toluene and 6.85 ml (0.016 mole) of a 25.2% strength suspension of trimethylaluminium in hexane.

The mixture is cooled, and 1.05 ml (0.016 mole), equivalent to 0.95 g, of ethylenediamine dissolved in 3 ml of toluene is then added.

While being stirred, the mixture is heated and, at about 50° C., there is added a solution of 2.5 g (0.0096 mole) of the oil prepared as above in 9 ml of toluene.

The mixture is heated under reflux, removing approximately 10 ml of solvent, to obtain an internal temperature of 110° C. After 8 hours of heating, the mixture is cooled to approximately −15° C. and hydrolysed with 6.6 ml of water.

The mixture is stirred for 10 minutes and then extracted with ethyl acetate, and the organic phase is washed with saturated sodium chloride solution, dried, filtered and evaporated. There remains a yellow oil, the fumarate of which is prepared directly.

For this purpose, 2.5 g (0.0096 mole) of this oil are dissolved in 25 ml of ethanol, and the solution is filtered and mixed with a filtered solution of 0.9 g (0.008 mole) of fumaric acid in 50 ml of ethanol.

After 15 minutes of stirring, the mixture is evaporated under vacuum on a water bath, and the residue is taken up in acetone. The crystals formed are drained and rinsed, dried under vacuum and recrystallised in ethanol. The product melts at 212°–213° C.

EXAMPLE 5

2-(4,5-Dihydro-1H-imidazol-2-yl)-8-fluoro1,2,5,6-tetrahydro-4H-pyrrolo[3,2,1-ij]quinoline and its fumarate (a) In a 1-liter 3-necked flask, equipped with a reflux condenser, magnetic stirrer, thermometer and hydrogen chloride gas inlet and placed in a bath of dry ice and isopropyl alcohol, there are introduced 18.52 g (0.075 mole) of ethyl 5,6-dihydro-8-fluoro-4H-pyrrolo[3,2,1-ij]quinoline-2-carboxylate and 160 ml of ethanol. The mixture is cooled to −60° C., and hydrogen chloride gas is then condensed in until the starting ester has completely dissolved. 28.72 g (0.24 g-at.) of granulated tin are then added and the mixture is stirred for 20 hours at 20° C.

The solvent is evaporated under vacuum, the residue is taken up in 500 ml of ethanol and the mixture is saturated with ammonia until pH 9< is attained.

The suspension is filtered and the solvent evaporated from the filtrate. 200 ml of water are added and the mixture is extracted with 600 ml of ether; the ether phase is washed with water, then with water saturated with sodium chloride and dried over magnesium sulphate, and the ether is evaporated under vacuum. Ethyl 1,2,5,6-tetrahydro-8-fluoro-4H-pyrrolo[3,2,1-ij]quinoline-2-carboxylate is obtained in the form of an oil.

(b) In a 150-ml three-necked flask, equipped with a magnetic stirrer, condenser and argon inlet, 21 ml of toluene are introduced and 25 g (13.7 ml, equivalent to 0.032 mole) of 25.2% strength trimethylaluminium in hexane are added. The solution is cooled to −10° C. and 1.92 g (0.032 mole) of ethylenediamine dissolved in 6 ml of toluene is added, and there are then added at 20° C. 3.73 g (0.015 mole) of the ester obtained as above dissolved in 20 ml of toluene. The mixture is stirred at 110° C. for 4 hours and cooled to −10° C., and 10 ml of water and 50 ml of ethyl acetate are added slowly.

The mixture is stirred at 20° C. for 30 minutes and filtered, and the organic phase is separated, washed and dried, and the ethyl acetate is evaporated.

The base thus obtained is taken up in 20 ml of ethanol and a solution of 0.7 g of fumaric acid in 20 ml of ethanol is added. The whole mixture is stirred for 15 minutes and the alcohol is driven off under vacuum. The fumarate obtained melts at 182°–185° C.

The table which follows illustrates the other compounds prepared according to the invention.

TABLE

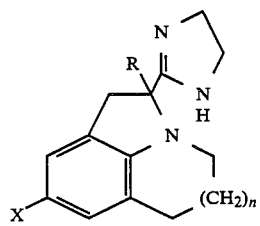

(I)

| Compound | Example | R | X | n | M.p. (°C.) | Base/salt(*) |
|---|---|---|---|---|---|---|
| 1 | 1 | H | H | 1 | 186–188 | 08 |

TABLE-continued

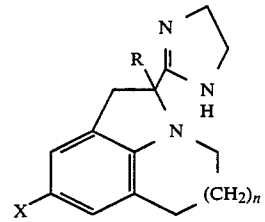

(I)

| Compound | Example | R | X | n | M.p. (°C.) | Base/salt(*) |
|---|---|---|---|---|---|---|
| 2 | 2 | —CH$_3$ | H | 1 | 184.5–186 | 08 |
| 3 | | —CH$_2$CH$_3$ | H | 1 | 182–184 | 08 |
| 4 | | —CH$_2$CH$_2$CH$_3$ | H | 1 | 218–220 | 08 |
| 5 | | —CH$_2$CH=CH$_2$ | H | 1 | 195–197 | 08 |
| 6 | 3 | H | H | 2 | 108–140 | 08 |
| 7 | 4 | —CH$_3$ | H | 2 | 212–213 | 08 |
| 8 | | —CH$_2$CH$_2$CH$_3$ | H | 2 | 197–199 | 08 |
| 9 | 5 | H | F | 1 | 182–185 | 08 |
| 10 | | —CH$_3$ | F | 1 | 199–202 | 08 |
| 11 | | —CH$_2$CH$_2$CH$_3$ | F | 1 | 210–212 | 08 |
| 12 | | —CH$_2$CH$_2$CH$_3$ | CH$_3$ | 1 | 198–200 | 08 |
| 13 | | H | CH$_3$ | 1 | 173–175 | 08 |
| 14 | | —CH$_3$ | CH$_3$ | 1 | 154–158 | 08 |
| 15 | | H | Cl | 1 | 195–196 | 08 |
| 16 | | —CH$_3$ | Cl | 1 | >260 | 10 |
| 17 | | H | OCH$_3$ | 1 | 144–147 | 08 |

(*)08: fumarate
10: hydrochloride

The compounds of the invention were subjected to pharmacological tests which showed their value as $\alpha_2$-antagonists.

To this end, the compounds were studied in the test of potentiality and selectivity of antagonists towards $\alpha_2$-receptors in vitro.

Determination of the pA$_2$ value in respect of the inhibitory effects of clonidine, a well-known $\alpha_2$-agonist, was carried out on rat vas deferens stimulated at a frequency of 0.1 Hz in the presence of 300 nM prazosin and 1 μM cocaine, according to the method described by G. M. Dre (European Journal of Pharmacology, 42, (1977) 123–130).

The pA$_2$ of the compounds of the invention range from 6.0 to 9.0.

The compounds of the invention are $\alpha_2$-antagonists which can be used for the treatment of depression (either alone or in association with products which inhibit neuronal uptake mechanisms), hypotension, post-operative paralytic ileum, asthma and obesity.

The pharmaceutical compositions of the invention can be in a form suitable for oral, rectal or parenteral administration, for example in the form of capsules, tablets, pellets, gelatine capsules or solutions, syrups or suspensions to be taken orally, and can contain suitable excipients.

The daily dose can range from 0.1 to 20 mg/kg taken orally.

We claim:

1. An imidazoline derivative, in the form of an enantiomer or a mixture thereof, of the formula (I)

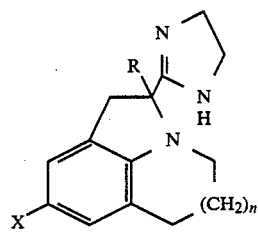

in which n is 1 or 2, R is hydrogen, $C_1$-$C_3$ alkyl or allyl, and X is hydrogen, halogen, methyl or methoxy, or a pharmaceutically acceptable acid addition salts thereof.

2. A pharmaceutical composition for treating depression comprising an anti-depressant effective amount of an imidazoline derivative or salt as claimed in claim 1 and a pharmaceutically acceptable diluent therefor.

3. A pharmaceutical composition for treating asthma comprising an asthma treating effective amount of an imidazoline derivative or salt as claimed in claim 1 and a pharmaceutically acceptable diluent therefor.

4. A pharamaceutical composition for treating obesity comprising a weight-lowering effective amount of an imidazoline derivative or salt as claimed in claim 1 and a pharmaceutically acceptable diluent therefor.

* * * * *